US012661380B2

(12) United States Patent
Laza Knoerr et al.

(10) Patent No.: US 12,661,380 B2
(45) Date of Patent: Jun. 23, 2026

(54) COMPOSITION FOR THE NUTRITION OR DRINK OF A NON-HUMAN ANIMAL

(71) Applicant: AGRO INNOVATION INTERNATIONAL, Saint-Malo (FR)

(72) Inventors: Anca L. Laza Knoerr, Saint-Malo (FR); Sandra Point, Plerguer (FR); Auriane De Tonnac, Bruz (FR); Philippe Dumargue, Ploufragan (FR)

(73) Assignee: AGRO INNOVATION INTERNATIONAL, Saint-Malo (FR)

( * ) Notice: Subject to any disclaimer, the term of this patent is extended or adjusted under 35 U.S.C. 154(b) by 358 days.

(21) Appl. No.: 18/263,992

(22) PCT Filed: Feb. 7, 2022

(86) PCT No.: PCT/FR2022/050226
§ 371 (c)(1),
(2) Date: Aug. 2, 2023

(87) PCT Pub. No.: WO2022/167772
PCT Pub. Date: Aug. 11, 2022

(65) Prior Publication Data
US 2024/0115633 A1    Apr. 11, 2024

(30) Foreign Application Priority Data
Feb. 8, 2021    (FR) ....................................... 2101179

(51) Int. Cl.
| | |
|---|---|
| *A61K 35/748* | (2015.01) |
| *A23K 10/16* | (2016.01) |
| *A23K 10/30* | (2016.01) |
| *A23K 50/30* | (2016.01) |
| *A23K 50/60* | (2016.01) |
| *A23K 50/75* | (2016.01) |
| *A61K 36/03* | (2006.01) |
| *A61P 1/14* | (2006.01) |

(52) U.S. Cl.
CPC ............ *A61K 35/748* (2013.01); *A23K 10/16* (2016.05); *A23K 10/30* (2016.05); *A23K 50/30* (2016.05); *A23K 50/60* (2016.05); *A23K 50/75* (2016.05); *A61K 36/03* (2013.01); *A61P 1/14* (2018.01)

(58) Field of Classification Search
CPC ...... A61K 35/748; A61K 36/03; A23K 10/16; A23K 10/30; A23K 50/30; A23K 50/60; A23K 50/75; A61P 1/14; A23L 33/105
See application file for complete search history.

(56) References Cited

FOREIGN PATENT DOCUMENTS

| | | |
|---|---|---|
| DE | 19608563 A1 | 10/1997 |
| DE | 19906016 A1 * | 8/2000 |
| EP | 1570845 A1 | 9/2005 |
| IT | PD20110179 A1 | 11/2012 |
| JP | 2019170339 A * | 10/2019 |
| KR | 20200129841 A | 11/2020 |
| WO | 200122822 A1 | 4/2001 |
| WO | 2004080196 A2 | 9/2004 |

OTHER PUBLICATIONS

El-Naga et al., Egyptian J. Nutrition and Feeds, 2018, vol. 21, No. 2, p. 495-507. DOI: 10.21608/ejnf.2018.75603. (Year: 2018).*
Zhao et al. (2019), PLoS One 14(6): e0218543. doi.org/10.1371/journal. pone.0218543. (Year: 2019).*
Rattigan et al., Mar. Drugs, 2019, 17, 680; doi: 10.3390/md17120680. (Year: 2019).*
Makkar et al., "Seaweeds for livestock diets: A review", Animal Feed Science and Technology, 2016, vol. 212, pp. 1-17.
Praveen et al., "An overview of extraction and purification techniques of seaweed dietary fibers for immunomodulation on gut microbiota", Trends in Food Science and Technology, 2019, vol. 92, pp. 46-64.
Belay et al., "Spirulina (Arthrospira): Potential application as an animal feed supplement", Journal of Applied Phycology, 1996, vol. 8, No. 4-5, pp. 303-311.
Frédéric Vernier (Authorized Officer), International Search Report dated Mar. 29, 2022 for corresponding International Application No. PCT/FR2022/050226, 7 pages with English Translation.
French Search Report and Written Opinion dated Sep. 28, 2021 for corresponding French Application No. 2101179, 10 pages.

* cited by examiner

*Primary Examiner* — Kade Ariani
(74) *Attorney, Agent, or Firm* — MH2 Technology Law Group, LLP

(57) ABSTRACT

The present invention relates to a composition for the nutrition or drink of a non-human animal comprising the combination of *spirulina* and *Ascophyllum nodosum*. It further relates to the use of this composition for improving the zootechnical performance of non-human animals.

10 Claims, 8 Drawing Sheets

[Fig. 1]
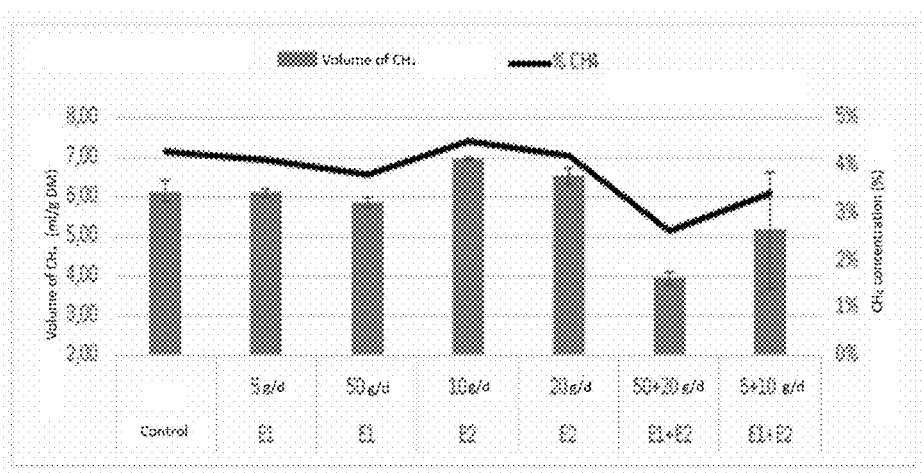
[Fig. 2]
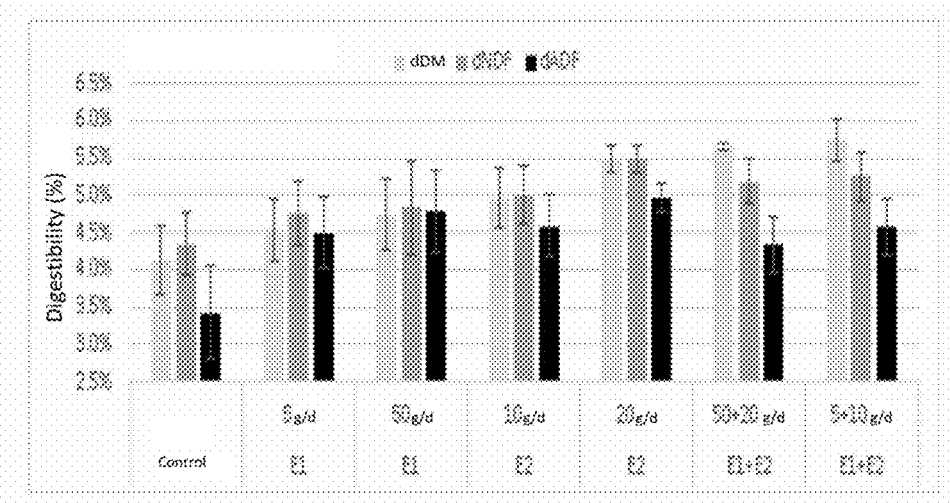

[Fig. 3]
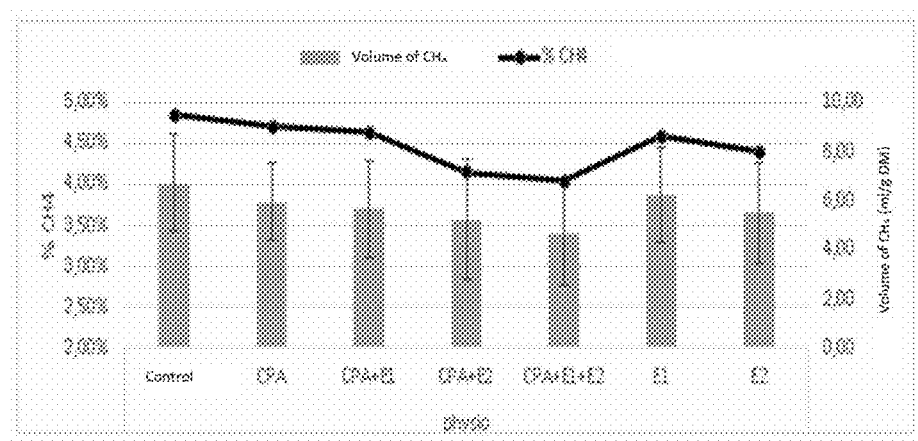
[Fig. 4]
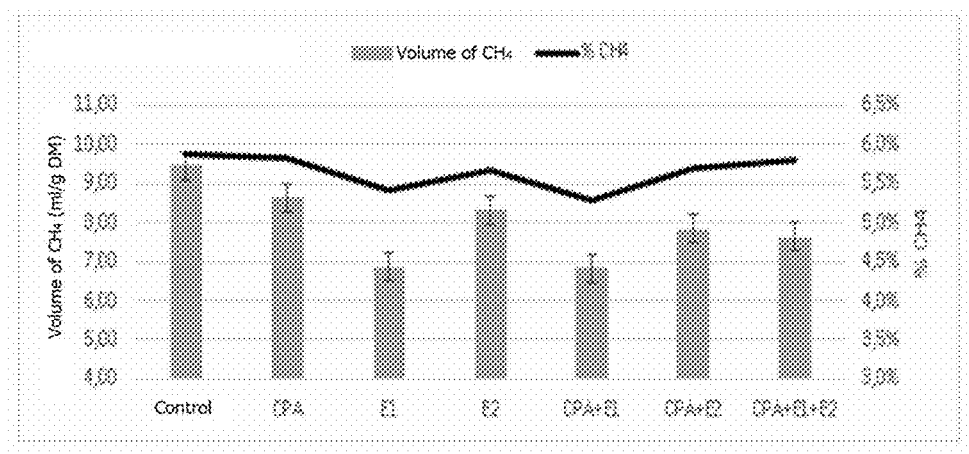

[Fig. 5]
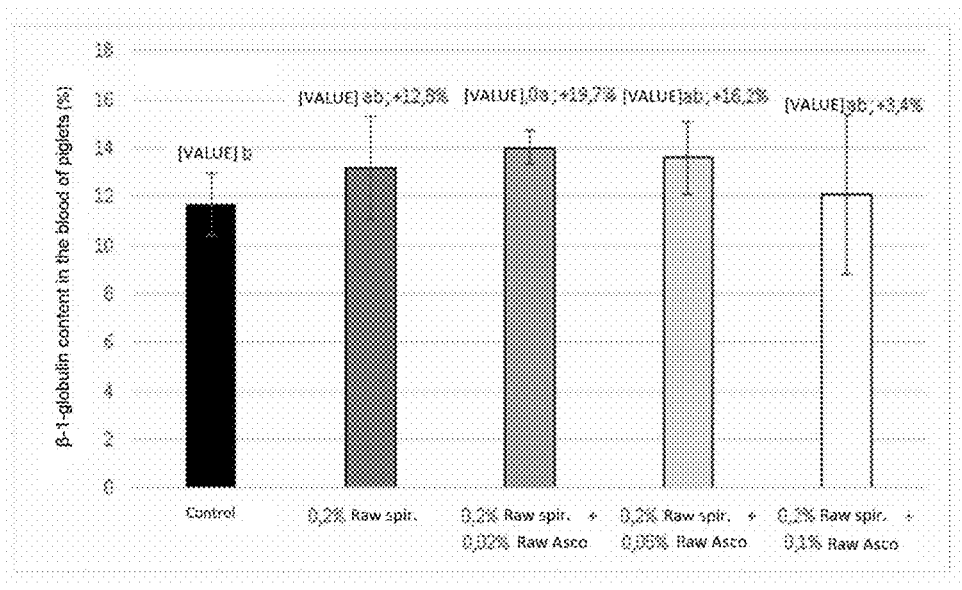
[Fig. 6]
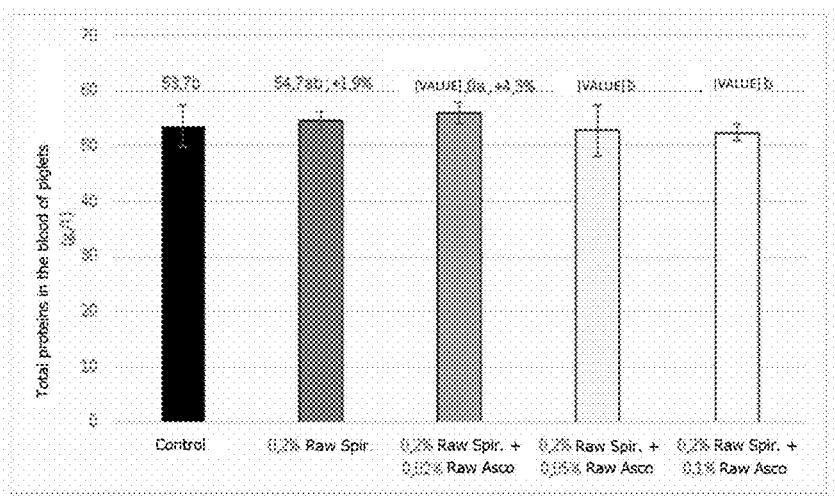

[Fig. 7]
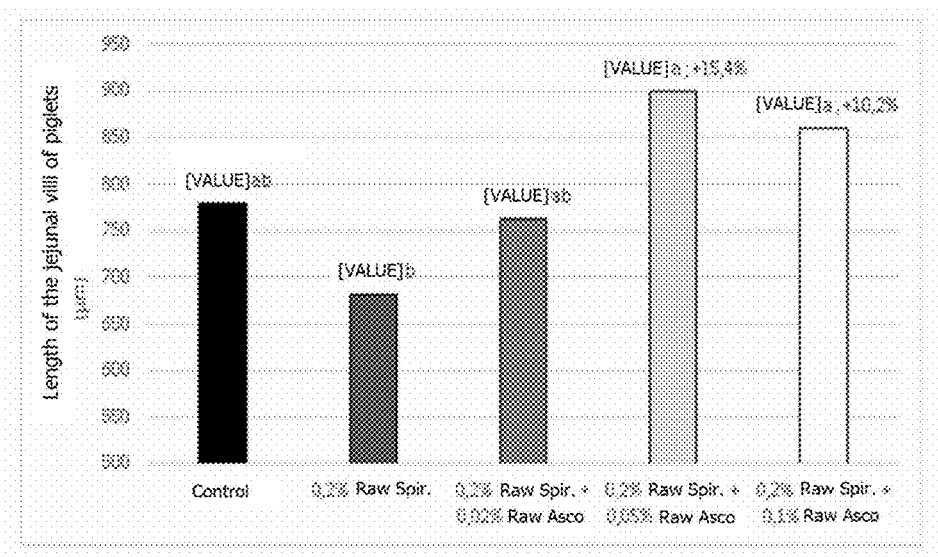
[Fig. 8]
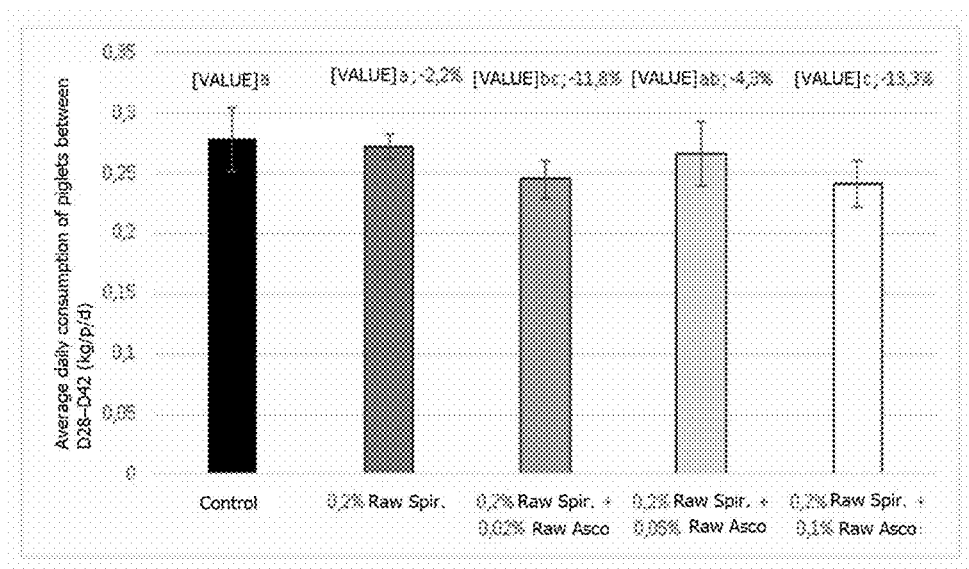

[Fig. 9]
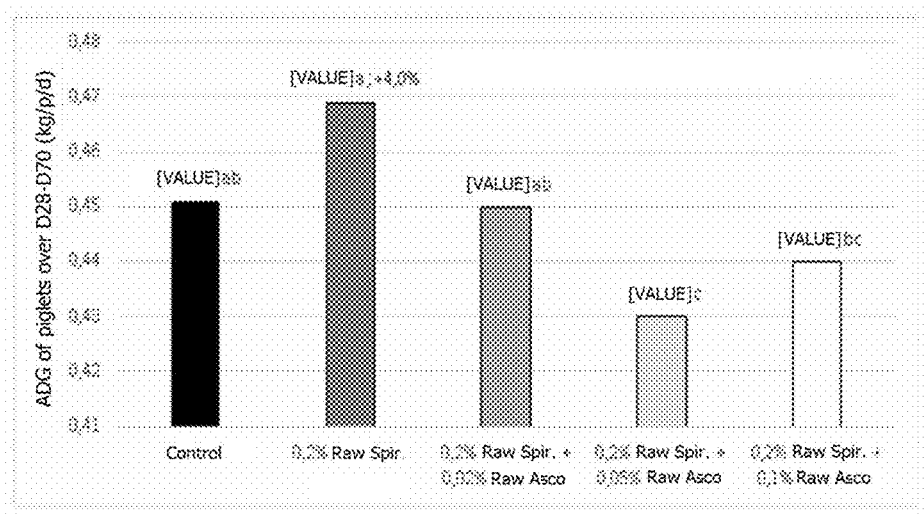
[Fig. 10]
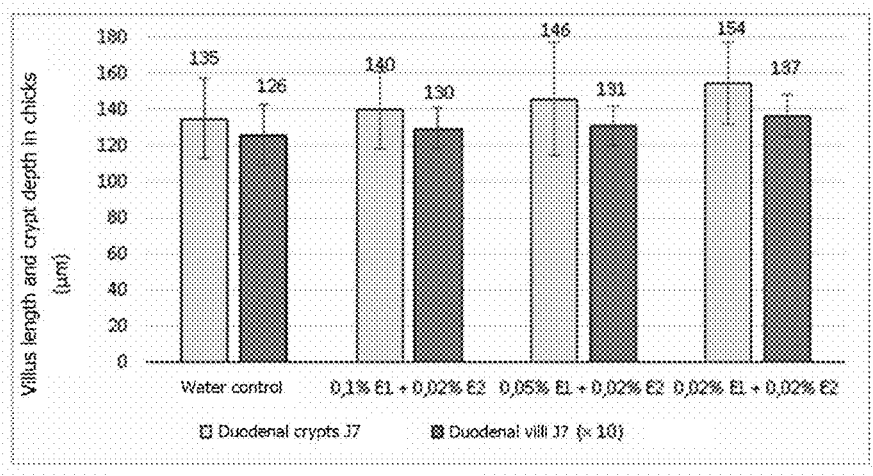

[Fig. 11]
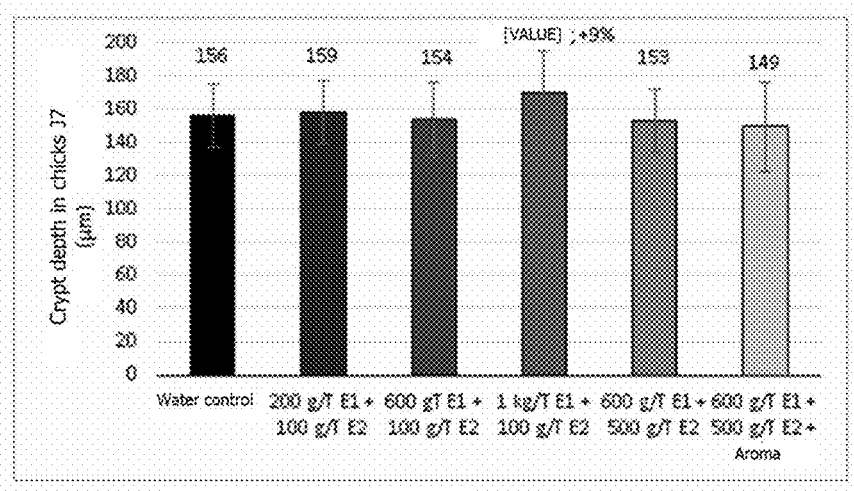
[Fig. 12]
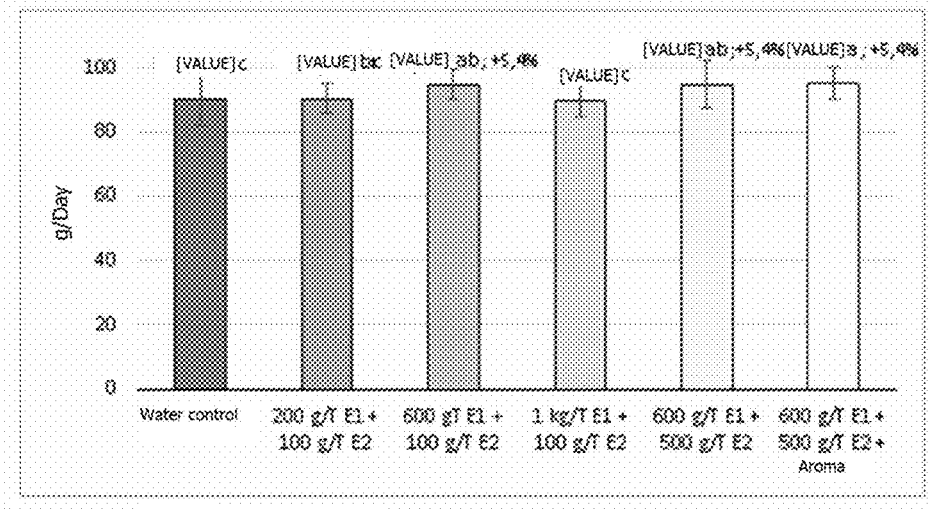

[Fig. 13]
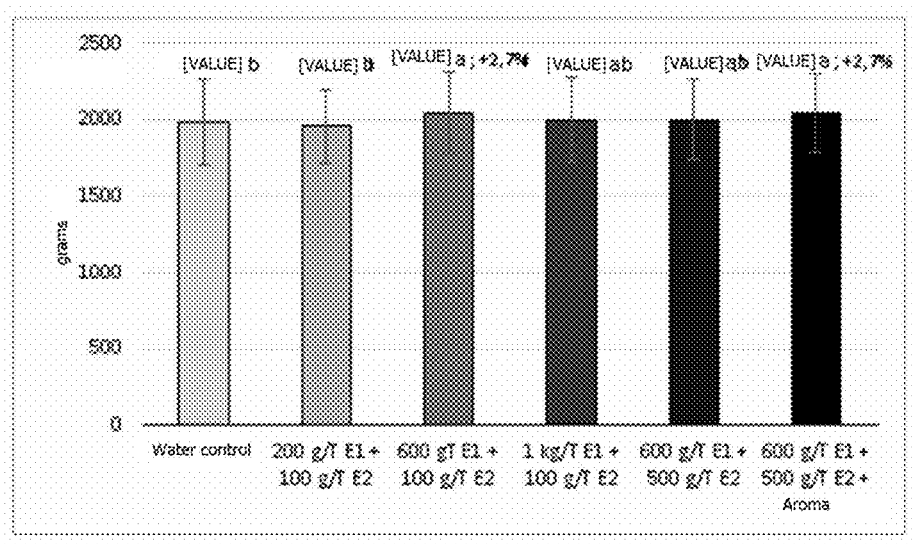
[Fig. 14]
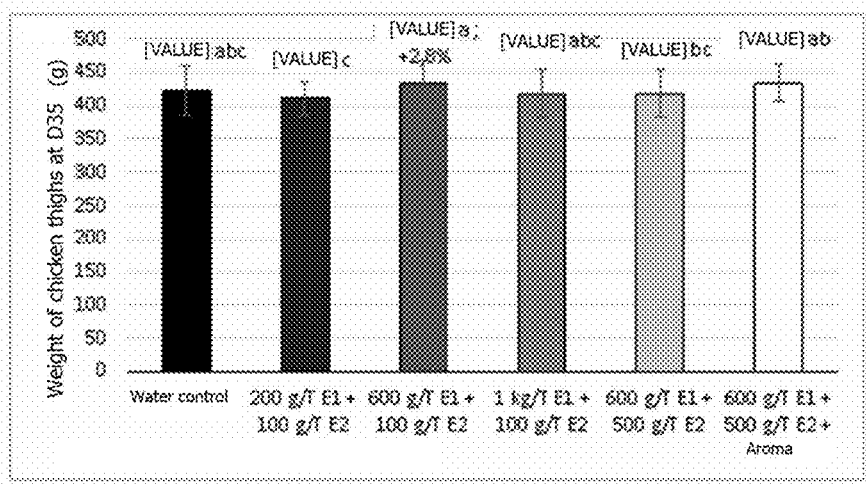

[Fig. 15]
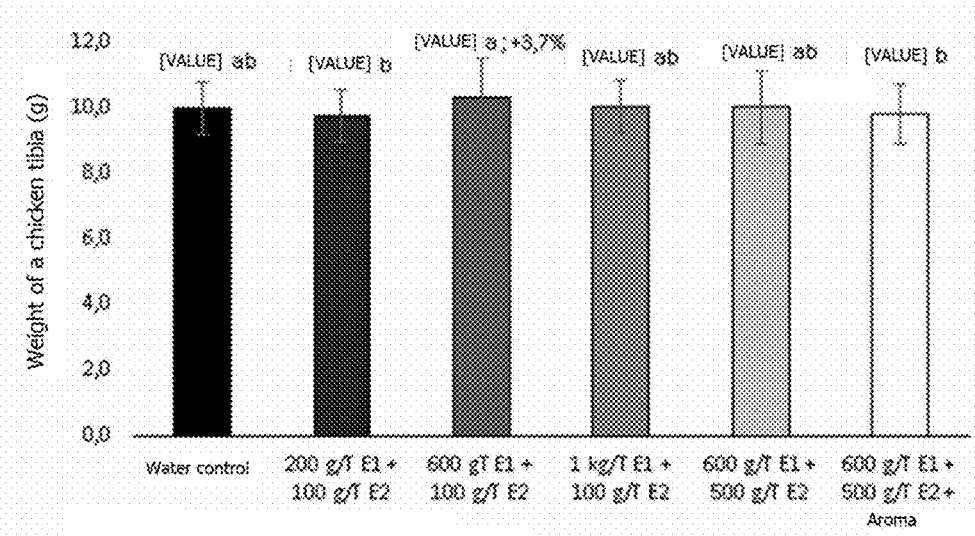
[Fig. 16]
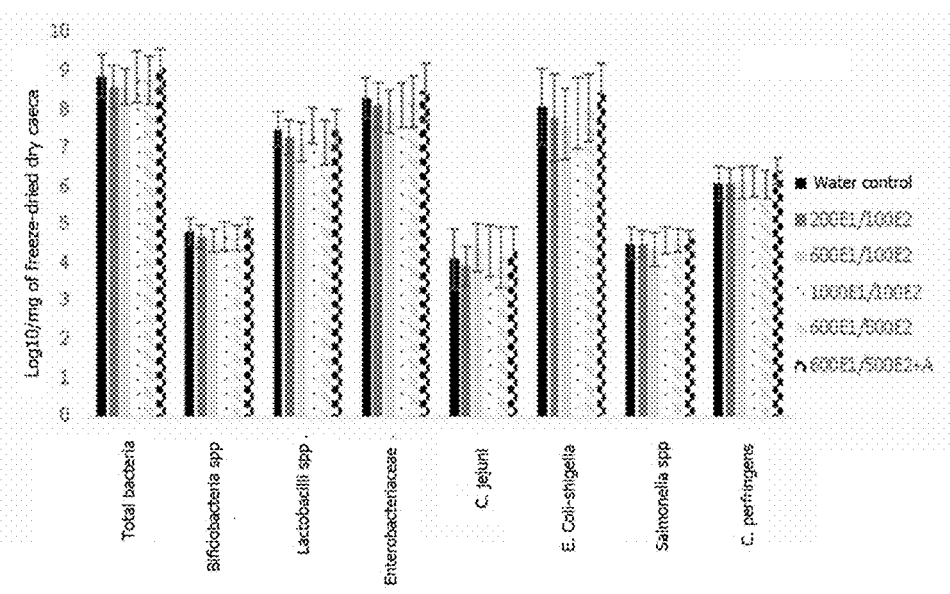

COMPOSITION FOR THE NUTRITION OR DRINK OF A NON-HUMAN ANIMAL

CROSS-REFERENCE TO RELATED APPLICATIONS

This application is a national stage application of PCT/FR2022/050226 filed 7 Feb. 2022, which claims priority to French Patent Application No. 2101179 filed 8 Feb. 2021, the entire disclosures of each application are herein incorporated by reference.

TECHNICAL FIELD

The present invention relates to the field of non-human animal food and/or drink, and in particular the combination of *spirulina* and *Ascophyllum nodosum* algae or their extracts with a view to non-human animal food and/or drink, in particular for farm animals, more particularly livestock animals.

PRIOR ART

Application WO 2004/080196 describes the use of products derived from macroalgae, microalgae, plants and/or fungi in animal feed, replacing products derived from animals, in particular fish, because of their high content of LC-PUFAs (long chain polyunsaturated fatty acids) such as DHA (docosahexaenoic acid) and EPA (eicosapentaenoic acid). Among the microalgae mention is made of *spirulina* and among the macroalgae, *Ascophyllum*. However, these algae are mentioned among a long list of other possible microalgae or macroalgae. Furthermore, no specific example comprises the mixture of these two algae. Moreover, these algae are not used raw or in the form of an extract, but in the form of derivative products. Application WO 2001/22822 describes the use of a composition comprising a cytokine derived from *Ascophyllum nodosum* mixed with mineral-based nutrients, a mixture of vitamin B and acetyl salicylic acid or one of its salts, in the form of a drink or an injection solution, to improve the immunity of animals. The cytokine from *Ascophyllum nodosum* is obtained by extraction which uses a very specific method. The application describes the possible presence in the composition of other ingredients such as *spirulina*, which is mentioned in a long list of ingredients, without any example of combination of these two algae (*Ascophyllum nodosum* and *spirulina*) is disclosed.

Patent application EP1570845 describes the use of acidic polysaccharides as an agent to enhance bone morphogenetic protein production or enhance osteogenesis. The acid polysaccharide can be derived from algae such as among others *spirulina* or *Ascophyllum nodosum*. However, this document does not disclose any specific example containing acidic polysaccharides, in particular sulfated polysaccharides originating from both *Ascophyllum nodosum* and *spirulina*.

Application KR2020-0129841 describes in its examples ([0051]-[0059]) an animal model (rat) to which an aqueous extract of *spirulina* (SP at 800 mg/kg/day) or Ascophilum *Nodosum* (AN at 100 mg/kg/day or 200 mg/kg/day) mixed with water. However, the aqueous extracts of *spirulina* and Ascophilum *Nodosum* are used separately. Furthermore, their use is not for the improvement of well-being in an animal but for reducing or eliminating the toxicity of the lead ingested by the animals, the aim of these tests being to obtain a drug for human beings.

Furthermore, although this application does indeed describe aqueous extracts of *spirulina* or Ascophilum *Nodosum* ([0032]) used in animal drinks, it does not describe a protein extract of *spirulina* (and even less a protein hydrolyzate) nor polysaccharide extract of Ascophilum *Nodosum*. Finally, rats are not farm animals and even less livestock animals. Patent application DE 19608563 describes food compositions comprising the combination of raw *spirulina* and raw Ascophilum *Nodosum* and lithothamnium.

However, it is nowhere indicated in this application that these compositions are intended for animal feed, in particular farm animals and even less livestock animals.

These compositions are in fact intended for humans in whom they have been tested (examples).

Application ITPD20-110179 describes a composition for controlling dysglycemia in an animal.

However, it is not a farm animal and even less a livestock animal (such as poultry, ruminant animals, pigs and/or aquatic animals) but a domestic animal of the cat or dog type.

Indeed, farm animals do not suffer from dysglycemia. It is a typical pet disease. The composition described in this application is therefore not suitable for farm animals or livestock animals.

Furthermore, the composition described in this application must contain a *Gymnema Sylvestre* extract, a *Momordica Charantia* extract and zinc, which is not the case with the composition according to the invention.

Furthermore, this application does not describe an extract of *spirulina* or Ascophilum *Nodosum*, even less a protein extract of *spirulina* (and even less a protein hydrolyzate) or a polysaccharide extract of Ascophilum *Nodosum*. However, the inventors surprisingly realized that the combination of *Ascophyllum nodosum* and *spirulina*, whether in raw form or more advantageously in the form of an extract, in particular of polysaccharide extract of *Ascophyllum nodosum* and *spirulina* protein extract, had a synergistic action to improve the zootechnical performance of non-human animals, in particular farm animals, more particularly livestock animals, advantageously of a ruminant and/or a monogastric animal such as a bird or a pig and/or an aquatic animal such as a fish or a crustacean, but also domestic animals such as cats and dogs, when the combination was administered in a food composition or a drink.

DISCLOSURE OF THE INVENTION

The present invention therefore relates to a composition for the nutrition or drink of a non-human animal, in particular of a farm animal, more particularly livestock animal, advantageously of a ruminant and/or of a monogastric animal such as a poultry or a pig and/or an aquatic animal such as a fish or a crustacean, but also domestic animals such as cats and dogs, comprising the combination of *spirulina* and *Ascophyllum nodosum*.

The composition according to the invention therefore comprises *spirulina*. *Spirulina* is a microalga (35 μm wide and 200 μm long on average) recognizable by its particular spiral shape. Its scientific name is Arthrospira. It is a cyanobacterium belonging to the class Cyanophyceae (blue-green algae). Its color is due to the presence of phycocyanin (protein), a blue pigment used in particular in the food industry. There are nearly 1 500 species of blue algae and 36 species of *spirulina* are edible. The main species currently offered on the market is *Spirulina platensis*. The *spirulina* according to the invention is therefore advantageously *Spirulina platensis*. *Spirulina* contains proteins (including phycocyanin), various carotenoids (mainly beta-carotene, but also cryptoxanthin, lutein, zeaxanthin, etc.), vitamins and minerals including iron, magnesium, calcium, vitamins A, B, E. *Spirulina* further comprises a good content of essential amino acids (such as aspartic acid, threonine, serine, gluta- mic acid, proline, glycine, alanine, cystine, valine, methio- nine, isoleucine, leucine, tyrosine, phenylalanine, histidine, lysine and arginine) and gamma-linolenic acid, an unsatu- rated fatty acid from the omega-6 family. In particular, its protein content is comprised between 55 and 70% (limits included), advantageously greater than or equal to 60%, particularly between 60 and 70% (limits included), more advantageously between 65 and 69% (limits included), by weight relative to the total weight of the *spirulina.*

In addition, *spirulina* is rich in phycocyanin, the only natural blue pigment that can be used as a food coloring and to which a significant antioxidant activity is attributed, in particular its content is greater than or equal to 7%, more advantageously greater than or equal to 8%. It also contains chlorophyll.

The *spirulina* according to the invention can therefore be used raw, in particular dehydrated, more advantageously in powder form. Advantageously, it is not used in the form of a hydrogel. Even more advantageously, it does not contain mucilage. In a particularly advantageous embodiment, the *spirulina* according to the invention is not used in combi- nation with or in a composition containing a *Gymnema Sylvestre* extract and/or a *Momordica Charantia* extract and/or zinc.

However, in an advantageous embodiment, the *spirulina* is in the form of an extract, advantageously the extract does not contain acid polysaccharides, more advantageously it is a protein extract (in particular water-soluble), more advan- tageously a protein hydrolyzate.

In particular the extraction is carried out by maceration advantageously in an aqueous solvent, more advantageously water, more particularly in a content of 100 g of dehydrated *spirulina* in 900 g of solvent, in particular at a temperature comprised between 30 and 80° C. (limits included), more advantageously between 50 and 70° C. (limits included), in particular 60° C., for a duration advantageously comprised between 1 hour and 6 hours (limits included), more advan- tageously between 2 hours and 4 hours (limits included).

Advantageously, the protein hydrolyzate is obtained by hydrolysis of the protein extract, in particular by enzymatic hydrolysis, more advantageously using an endoprotease enzyme such as serine endoproteases such as for example subtilisin, advantageously marketed by Novozymes under the trade name Novo-Pro® D. The hydrolysis advanta- geously takes place in aqueous solution, in particular at a pH comprised between 7 and 11 (limits included), more par- ticularly between 7 and 10 (limits included), even more particularly between 8 and 9.5 (limits included), in particular 8, advantageously at a temperature comprised between 55 and 75° C. (limits included), more advantageously between 55 and 65° C. (limits included), in particular 60° C.

In an advantageous embodiment, the extract is in liquid form. The protein extract advantageously contains more than 70% by weight, in particular more than 72% by weight, of protein relative to the total weight of the dry matter of the extract.

The protein hydrolyzate advantageously contains poly- peptides, peptides and amino acids (such as aspartic acid, threonine, serine, glutamic acid, proline, glycine, alanine, cystine, valine, methionine, isoleucine, leucine, tyrosine, phenylalanine, histidine, lysine and arginine), advanta- geously the molecular weight of the polypeptides and peptides can range from less than 150 Da to more than 20 000 Da. Advantageously, the protein hydrolyzate comprises more than 85% by weight of polypeptides, peptides and amino acids having a molecular weight less than or equal to 5000 Da, advantageously more than 90% by weight, in particular more than 92% by weight relative to the total weight of polypeptides, peptides and amino acids of the protein hydrolyzate. Advantageously, the protein hydrolyz- ate comprises more than 70% by weight of polypeptides, peptides and amino acids having a molecular weight less than or equal to 1000 Da, advantageously more than 75% by weight, in particular more than 80% by weight, relative to the total weight of polypeptides, peptides and amino acids of the protein hydrolyzate. Advantageously, the protein hydro- lyzate comprises more than 50% by weight of polypeptides, peptides and amino acids having a molecular weight less than or equal to 500 Da, advantageously more than 60% by weight, in particular more than 65% by weight, relative to the total weight of polypeptides, peptides and amino acids of the protein hydrolyzate.

Advantageously, the composition according to the inven- tion comprises between 0.01 and 0.5% (limits included) by weight relative to the total weight of the composition, advantageously between 0.03 and 0.4% (limits included) by weight relative to the total weight of the composition, even more advantageously between 0.02 and 0.2% (limits included) by weight relative to the total weight of the composition, of *spirulina*, advantageously of *spirulina* extract, more advantageously of *spirulina* protein hydrolyz- ate. The *spirulina* content of the composition depends in particular on the animal for which the food or drink is intended.

Thus, in particular the composition according to the invention comprises 0.2% by weight relative to the total weight of the composition, of *spirulina*, advantageously of *spirulina* extract, more advantageously of *spirulina* protein hydrolyzate, when the composition is intended to porcines, more advantageously when it is intended for pigs or piglets, which are weaned or unweaned, in particular when it is intended for piglets, which are weaned or unweaned.

More particularly, the composition according to the invention comprises between 0.02% and 0.1% (limits included) by weight relative to the total weight of the composition, of *spirulina*, advantageously of *spirulina* extract, more advantageously of *spirulina* protein hydrolyz- ate, when the composition is intended for birds, in particular farm birds, more particularly for poultry, more advanta- geously when it is intended for gallinaceans such as chick- ens or chicks.

Advantageously, the content of *spirulina*, advantageously of *spirulina* extract, more advantageously of *spirulina* pro- tein hydrolyzate, administered to ruminant animals, in par- ticular to dairy cows, using the composition according to the invention, is comprised between 2 and 70 g/D (limits included), in particular between 5 and 50 g/D (limits included), more advantageously it is 5 g/D, for a ration of about 15 kg of fodder per day. The composition according to the invention further comprises *Ascophyllum nodosum.*

*Ascophyllum nodosum*, also known as knotted wrack, knotted kelp, is a macroalgae (it can reach more than 1.50 m in length) of brown color which belongs to the class of Phaeophyceae. It is the only representative, currently rec- ognized, of the genus *Ascophyllum*, in the family Fucaceae.

It contains high levels of macro-elements (such as N, P, K, Ca, Mg, S) and trace elements (for example Mn, Cu, Fe, Zn, etc.). It also contains phytohormones such as betaine, cytokinin, auxin and gibberellin (growth stimulators), mannitol, organic acids, polysaccharides, amino acids and proteins.

*Ascophyllum nodosum* according to the invention can therefore be used raw, in particular dehydrated, more advantageously in powder form. Advantageously, the *Ascophyllum nodosum* according to the invention is not used in the form of a hydrogel. Even more advantageously, it does not contain AOS (alginatooligosaccharides). In a particularly advantageous embodiment, the *Ascophyllum nodosum* according to the invention is not used in combination with or in a composition containing a *Gymnema Sylvestre* extract and/or a *Momordica Charantia* extract and/or zinc.

However, in an advantageous embodiment, the *Ascophyllum nodosum* is in the form of an extract, advantageously the extract contains no cytokine, more advantageously it is a polysaccharide extract (which is in particular water-soluble), more preferably the extract has been clarified, even more preferably dehydrated.

In particular the extraction is carried out by maceration advantageously in an aqueous solvent, more advantageously water, in particular in a content of 200 g of dehydrated *Ascophyllum nodosum* in 800 g of solvent, in particular at a temperature comprised between 30 and 95° C. (limits included), more advantageously between 45 and 90° C. (limits included), for a duration advantageously comprised between 1 hour and 6 hours (limits included), more advantageously between 2 hours and 4 hours (limits included).

In an advantageous embodiment, the extract is in liquid form. In an even more advantageous embodiment, it is in powder form.

Advantageously, the composition according to the invention comprises between 0.05 and 0.5% (limits included) by weight relative to the total weight of the composition, advantageously between 0.06 and 0.15% (limits included) by weight relative to the total weight of the composition, more advantageously between 0.01 and 0.1% (limits included) by weight relative to the total weight of the composition, of *Ascophyllum nodosum*, advantageously of *Ascophyllum nodosum* extract. The *Ascophyllum nodosum* content of the composition depends in particular on the animal for which the food or drink is intended.

In particular, the composition according to the invention comprises between 0.02% and 0.1% (limits included) by weight relative to the total weight of the composition, of *Ascophyllum nodosum*, advantageously of *Ascophyllum nodosum* extract, when the composition is intended for porcines, more advantageously when it is intended for pigs or piglets, which are weaned or unweaned, in particular when it is intended for piglets, which are weaned or unweaned.

More particularly, the composition according to the invention comprises between 0.01% and 0.05% (limits included) by weight relative to the total weight of the composition, of *Ascophyllum nodosum*, advantageously of *Ascophyllum nodosum* extract, when the composition is intended for birds, in particular for farm birds, more particularly for poultry, more advantageously when it is intended for gallinaceans such as chickens or chicks.

Advantageously, the content of *Ascophyllum nodosum*, advantageously of *Ascophyllum nodosum* extract, administered to ruminant animals, in particular to dairy cows, using the composition according to the invention, is comprised between 5 and 50 g/D (limits included), in particular between 10 and 20 g/D (limits included), more advantageously it is 10 g/D, for a ration of approximately 15 kg of fodder per day.

Advantageously the *spirulina/Ascophyllum nodosum* weight ratio, in particular the *spirulina* extract/*Ascophyllum nodosum* extract weight ratio, more advantageously the *spirulina* protein hydrolyzate/*Ascophyllum nodosum* extract weight ratio is comprised within the range 0.02-100 (limits included), advantageously 0.2-15 (limits included), in particular 0.5-20 (limits included) more particularly between 1/2-3/1 (limits included). This ratio depends in particular on the animal for which the food or drink is intended.

In particular, this ratio is comprised within the range 2-10 (limits included), when the composition is intended for porcines, more advantageously when it is intended for pigs or piglets, which are weaned or unweaned, in particular when it is intended for piglets, which are weaned or unweaned. More particularly, this ratio is comprised within the range 2-20 (limits included), when the composition is intended for birds, in particular for farm birds, more particularly for poultry, more advantageously when it is intended for gallinaceans such as chickens or chicks.

Advantageously, this ratio is comprised within the range 0.04-14 (limits included), advantageously 0.25-5 (limits included), more advantageously 0.5-2.5 (limits included), even more advantageously it is 0.5, when the composition is intended for ruminant animals, in particular dairy cows, more particularly having a daily ration of 15 kg of fodder.

The composition according to the invention is therefore intended for oral administration to animals. It may be a food composition or a drink, advantageously a food composition.

The composition according to the invention may further comprise lithothamnium. It may moreover comprise other ingredients known to the person skilled in the art for the nutrition or drink of animals, such as for example fodder in the case of ruminant animals or water in the case of drinks and/or cobs in the case of poultry.

In an advantageous embodiment, the composition according to the invention does not contain a *Gymnema Sylvestre* extract and/or a *Momordica Charantia* extract and/or zinc.

The composition according to the invention may have any form suitable for the food or drink of non-human animals, in particular a solid form, a powder or granule form or a liquid or gel form.

It can thus be added directly to the ration of non-human animals, or be added to premixes or food supplements or to nutritional blocks or buckets. In an advantageous embodiment, it is added to the daily ration of a non-human animal, in particular of a ruminant animal such as for example a dairy cow, advantageously at the rate of 5 mg/day of composition for 1 kg of the ration dry matter.

For ruminant animals, this ration can for example be made up of fodder of all types and in all its forms (green, dehydrated, ensiled, agglomerated, etc.) such as grass and other fodder grasses, fodder cereals (barley, corn, oats, wheat, sorghum, soybeans, rye), legumes (peas, *faba* beans, lupins, soybeans, alfalfa, sainfoin, clovers), roots, tubers and their by-products (beets, beet pulp, potato, potato pulp, etc.), cabbage, rapeseed, sunflower, plant waste (haulms, cobs, cereal husks, bran, shelled corncobs, bagasse) and starches, by-products of food industry (starch manufacture, ethanol manufacture, brewery, milling, etc.), as well as oilseed cakes, syrups, and nitrogenous food materials such as urea and its derivatives (biuret, ureides) and ammoniacal salts.

Preferably, the appropriate ration for ruminant animals according to the invention comprises fodder, preferably corn silage typically representing from 10 to 50% of the dry matter ingested, preferably daily, preferably combined with other fodder such as hay, straw or grass or cereal silage and preferably supplemented with concentrated feed such as cereals, oilseed cakes or compound feed.

In particular, it is a mixture of corn silage, hay and concentrates (consisting for example of wheat, corn, barley, beet pulp, wheat bran and molasses), for example in a 50:30:20 ratio, or of hay, concentrate and corn starch, for example in a 77:9:12:2 ratio.

The composition is intended for a non-human animal, in particular for a farm animal, more particularly for a livestock animal, advantageously a ruminant animal and/or a monogastric animal and/or an aquatic animal. In particular, it may be a mammal.

By "livestock animal" or "production animal" is meant within the meaning of the present invention any animal farmed or kept for its profitability, that is to say "the production of foodstuffs, wool, skins or other agricultural purposes".

Among the animals, the herbivores and in particular the ruminant animals are mammals which have a diet based on vegetable fibers containing, among the soluble fibers, insoluble fibers of the cellulose and hemicellulose type, fibers that are very poorly digestible.

The ruminant has the particularity of digesting via a "fermentation tank", the rumen (130-180 liters) interposed in the front part of the digestive tract. The rumen contains a wide variety of microflora of bacteria and protozoa which carry out a priority and very effective fermentation predigestion. The microbial flora therefore conditions the digestibility of carbohydrates, proteins, the self-supply of vitamins or other nutrients.

In an advantageous embodiment, the composition according to the present invention is intended for the nutrition and/or drinking of non-human mammals, in particular farm mammals, more particularly livestock, in particular herbivores (such as ruminant animals, horses, lagomorphs) and more particularly ruminant animals.

Ruminant animals include, for example, bovine, ovine, goats, cervidae and camelids.

The composition according to the present invention may also be intended for the nutrition and/or drinking of domestic non-human mammals such as cats or dogs. By "bovine" is meant within the meaning of the present invention a subfamily of Bovidae comprising several important species of farm animals. Bovines include in particular cow, in particular dairy cow, suckler cow, heifer, calf, grass-fed calf, young bull, beef, fattening beef, bull, buffalo, yak, gayal and banteng.

By "ovine" is meant within the meaning of the present invention the ruminant herbivores of the genus *Ovis*. Ovines include, in particular, mouflon, mutton, ewe, young ewe and lamb.

By "goat" is meant within the meaning of the present invention the ruminant herbivores of the genus Capra. Goats include in particular the nanny goat, the billy goat, the kid and the ibex.

By "cervidae" is meant within the meaning of the present invention the ruminant animals of the Cervidae family, wearing antlers. Cervidaes include in particular, deer, fawn, young stag, doe, baby deer, male roe deer, brocade, female roe deer, reindeer, male fallow deer, female fallow deer and elk.

By "camelid" is meant, within the meaning of the present invention, artiodactyl mammals of the Camelidae family. The camelids include in particular the dromedary, the male camel, the female camel, the llama and the alpaca.

In an advantageous embodiment, the ruminant animal according to the invention is bovine, in particular, it is selected from cows, in particular dairy cows, calf, grass-fed calf, suckling calf, beef and fattening beef and more particularly preferably the dairy cow.

In an advantageous embodiment, the composition according to the present invention is intended for the nutrition and/or drinking of an aquatic animal. Aquatic animals may comprise fish, in particular from freshwater, brackish water or saltwater, more particularly farmed, in particular commercial fish, such as salmon, trout, bass, carp, tilapia, crucian, catlas, rohu, sea bream, meager, turbot, sturgeon and pangas.

Aquatic animals can also comprise crustaceans such as shrimp or crayfish. In an advantageous embodiment, the composition according to the present invention is intended for the nutrition and/or drinking of non-human mammals, in particular farm mammals, more particularly livestock mammals, in particular monogastric animals, and more particularly *omnivore* animals (porcines).

By "porcine" is meant within the meaning of the present invention mammals of the family Suidae of the genus Sus. Porcines include in particular the butcher pig (or fattening pig), weaned or unweaned piglet, sows, boars and gilts.

In an advantageous embodiment, the composition according to the present invention is intended for the nutrition and/or drinking of birds, in particular domestic birds and more particularly farm birds, and even more particularly livestock birds and in particular poultry.

By "poultry" is meant within the meaning of the present invention domestic birds farmed by a human mammal. Poultry can belong to the order of gallinaceous or to that of palmipeds.

By "gallinaceous" or "palmiped" is meant, within the meaning of the present invention, animals whose flesh or egg-laying products are intended to be consumed by a human mammal. The gallinaceans comprise in particular the laying hen, the quail, the rooster, the turkey, the guinea fowl, the pigeon, the pheasant and more particularly the broiler chicken (including the chick). The palmipeds comprise in particular the duck and the goose.

The present invention further relates to the use of the composition according to the invention for improving the zootechnical performance of non-human animals, advantageously of a ruminant and/or a monogastric animal such as a bird, for example a poultry or an *omnivore* for example a pig and/or an aquatic animal such as a fish or a crustacean.

It also relates to the use of the composition according to the invention in order to reduce the emission of greenhouse gases, in particular methane, in a non-human mammal, advantageously in a ruminant animal.

It also relates to the use of the composition according to the invention in order to increase the digestibility of the dry matter and fibers, in particular forage and concentrates, and/or to improve the consumption index and/or the dietary efficiency and/or to promote weight gain and/or to increase the intensity of fermentation and of microbial metabolism and/or to inhibit flora protozoa and/or to reduce the degradation of proteins and/or to orient the fermentation towards the production of volatile fatty acids, in particular towards propionic acid, in a non-human mammal, advantageously in a ruminant animal.

In addition, it relates to the use of the composition according to the invention, in order to improve the quality of the meat and/or the growth performance and/or the well-being of a non-human animal, advantageously of a monogastric animal such as a bird, in particular a domestic bird and more particularly a poultry. In addition, it relates to the use of the composition according to the invention, to improve the well-being of a domestic non-human animal such as a cat or a dog.

Finally, it relates to a composition according to the invention, for its use for improving the intestinal health and/or the intestinal well-being and/or the immune system and/or the bone mineralization and/or the quality of the bone structure and/or as an antibacterial in non-human animals, advantageously ruminant animals and/or monogastric animals such as birds, for example poultry, or *omnivore* animals, for example pigs, and/or aquatic animals such as fish or crustaceans, in particular in chickens, chicks, pigs or piglets, but also of a domestic non-human animal such as a cat or a dog.

Advantageously, the use of this composition is to increase the intestinal villi, in particular the length of the jejunal villi and/or the depth of the duodenal crypts, of monogastric non-human animals such as birds, for example poultry, or *omnivore* animals, for example pigs, in particular chickens, chicks, pigs or piglets, and/or to modulate the inflammatory response and/or to avoid damage associated with post-weaning nutritional stress in monogastric mammals such as *omnivore* animals in particular pigs, more particularly piglets.

The present invention will be better understood in light of the description of the figures and the examples which follow, which are given by way of indication.

BRIEF DESCRIPTION OF THE DRAWINGS

FIG. 1 represents the concentration in % and the volume in ml/g of the dry matter (DM) of $CH_4$ after 24 hours of in vitro fermentation for a winter ration for the control, the *Spirulina platensis* protein hydrolyzate (E1) at 5 g/d or 50 g/d, the polysaccharide extract of *Ascophyllum nodosum* (E2) at 10 g/d or 20 g/d or the combination of *Spirulina platensis* protein hydrolyzate and polysaccharide extract of *Ascophyllum nodosum* (E1+E2 at 50 g/d+20 g/d or 5 g/d+10 g/d) under the conditions of Example 2.

FIG. 2 represents the digestibility of the dry matter (dDM), of ADF (dADF) and of NDF (dNDF) in % after 24 hours of in vitro fermentation for a winter ration for the control—and the composition according to the invention, the *Spirulina platensis* protein hydrolyzate (E1) at 5 g/d or 50 g/d, the polysaccharide extract of *Ascophyllum nodosum* (E2) at 10 g/d or 20 g/d or the combination of *Spirulina platensis* protein hydrolyzate and polysaccharide extract of *Ascophyllum nodosum* (E1+E2 at 50 g/d+20 g/d or 5 g/d+10 g/d) under the conditions of Example 2.

FIG. 3 represents the concentration in % and the volume in ml/g of the dry matter (DM) of $CH_4$ after 24 hours of in vitro fermentation for a winter ration with an acidogen for the control, lithothamne (CalseaPowder Advance CPA) at 80 g/d, the *Spirulina platensis* protein hydrolyzate (E1) at 5 g/d, the polysaccharide extract of *Ascophyllum nodosum* (E2) at 10 g/d, the combination (simple mixture) of lithothamne and *Spirulina platensis* protein hydrolyzate (CPA+E1 at 80 g/d+5 g/d), the combination (simple mixture) of lithothamne and polysaccharide extract of *Ascophyllum nodosum* (CPA+E2 at 80 g/d+10 g/d) or the combination (simple mixture) of lithothamnium, *Spirulina platensis* protein hydrolyzate and polysaccharide extract of *Ascophyllum nodosum* (CPA+E1+E2 at 80 g/d+5 g/d+10 g/d) under the conditions of Example 2.

FIG. 4 represents the concentration in % and the volume in ml/g of the dry matter (DM) of $CH_4$ after 24 hours of in vitro fermentation for a winter ration with an acidogen for the control, lithothamne (CalseaPowder Advance CPA) at 80 g/d, the *Spirulina platensis* protein hydrolyzate (E1) at 5 g/d, the polysaccharide extract of *Ascophyllum nodosum* (E2) at 10 g/d, the combination (impregnation of the extract on the lithothamne) of lithothamne and *Spirulina platensis* protein hydrolyzate (CPA+E1 at 80 g/d+5 g/d), the combination (impregnation of the extract on the lithothamne) of lithothamne and polysaccharide extract of *Ascophyllum nodosum* (CPA+E2 at 80 g/d+10 g/d) or the combination (impregnation of extracts on the lithothamne) of lithothamne, *Spirulina platensis* protein hydrolyzate and polysaccharide extract of *Ascophyllum nodosum* (CPA+E1+E2 at 80 g/d+5 g/d+10 g/d) under the conditions of Example 2.

FIG. 5 represents the Beta-globulin content in the blood (%) of the piglets at D70 having received the control food (Control T1), raw *Spirulina platensis* at 0.2% (0.2% Raw Spir. T2), the combination of raw *Spirulina platensis* and raw *Ascophyllum nodosum* at 0.2% and 0.02% respectively (0.2% Raw Spir.+0.02% Raw Asco T3), at 0.2% and 0.05% respectively (0.2% Raw Spir.+0.05% Raw Asco T4) or 0.2% and 0.1% respectively (0.2% Raw Spir.+0.1% Raw Asco T5) under the conditions of Example 3. The letters a, b or c associated with the figures indicate the significant differences between treatments at 5% confidence. The percentage values indicate the range of improvement over the control.

FIG. 6 represents the amount of total blood proteins in g/l of blood of the piglets at D70 having received the control food (Control T1), raw *Spirulina platensis* at 0.2% (0.2% Raw Spir. T2), the combination of raw *Spirulina platensis* and raw *Ascophyllum nodosum* at 0.2% and 0.02% respectively (0.2% Raw Spir.+0.02% Raw Asco T3), at 0.2% and 0.05% respectively (0.2% Raw Spir.+0.05% Raw Asco T4) or 0.2% and 0.1% respectively (0.2% Raw Spir.+0.1% Raw Asco T5) under the conditions of Example 3. The letters a, b or c associated with the figures indicate the significant differences between treatments at 5% confidence. The percentage values indicate the range of improvement over the control.

FIG. 7 represents the length of the jejunal villi in micrometers of the piglets at D70 having received the control food (Control T1), raw *Spirulina platensis* at 0.2% (0.2% Raw Spir. T2), the combination of raw *Spirulina platensis* and raw *Ascophyllum nodosum* at 0.2% and 0.02% respectively (0.2% Raw Spir.+0.02% Raw Asco T3), at 0.2% and 0.05% respectively (0.2% Raw Spir.+0.05% Raw Asco T4) or 0.2% and 0.1% respectively (0.2% Raw Spir.+0.1% Raw Asco T5) under the conditions of Example 3. The letters a, b or c associated with the figures indicate the significant differences between treatments at 5% confidence. The percentage values indicate the range of improvement over the control.

FIG. 8 represents the average daily consumption over the $1^{st}$ age phase between D28 and D42 in kg/piglet/d of the animals having received the control food (Control T1), the raw *Spirulina platensis* at 0.2% (0.2% Raw Spir. T2), the combination of raw *Spirulina platensis* and raw *Ascophyllum nodosum* at 0.2% and 0.02% respectively (0.2% Raw Spir.+0.02% Raw Asco T3), at 0.2% and 0.05% respectively (0.2% Raw Spir.+0.05% Raw Asco T4) or 0.2% and 0.1% respectively (0.2% Raw Spir.+0.1% Raw Asco T5) under the conditions of Example 3. The letters a, b or c associated with the figures indicate the significant differences between treatments at 5% confidence. The percentage values indicate the range of improvement over the control.

FIG. 9 represents the average daily gain (ADG) over the $1^{st}$ age phase between D28 and D710 in kg/piglet/d of the animals having received the control food (Control T1), the raw *Spirulina platensis* at 0.2% (0.2% Raw Spir. T2), the combination of raw *Spirulina platensis* and raw *Ascophyllum nodosum* at 0.2% and 0.02% respectively (0.2% Raw Spir.+0.02% Raw Asco T3), at 0.2% and 0.05% respectively (0.2% Raw Spir.+0.05% Raw Asco T4) or 0.2% and 0.1% respectively (0.2% Raw Spir.+0.1% Raw Asco T5) under the conditions of Example 3. The letters a, b or c associated with the figures indicate the significant differences between treatments at 5% confidence. The percentage values indicate the range of improvement over the control.

FIG. 10 represents the length of the duodenal villi and depth of the duodenal crypts in micrometers of 7-day-old chicks having received normal drinking water (control: water) or water mixed with *Spirulina platensis* protein hydrolyzate (E1) and the polysaccharide extract of *Ascophyllum nodosum* (E2) at 0.1% of E1+0.02% of E2, 0.05% of E1+0.02% of E2 or 0.02% of E1+0.02% of E2 respectively under the conditions of Example 4.

FIG. 11 represents the depth of the duodenal crypts in micrometers measured in 7-day-old chicks having received a normal diet (control: cob+water—T1) or a food provided with cob mixed with the *Spirulina platensis* protein hydrolyzate (E1) and the polysaccharide extract of *Ascophyllum nodosum* (E2) at 200 g/T of food of E1+100 g/T of food of E2 (T2), 600 g/T of E1+100 g/T of E2 (T3), 1000 g/T of E1+100 g/T of E2 (T4), 600 g/T of E1+500 g/T of E2 (T5) or 600 g/T of E1+500 g/T of E2+Aroma (T6) respectively under the conditions of Example 4. The percentage values indicate the range of improvement over the control.

FIG. 12 represents the average daily gain (ADG) over the phase between D27 and D35 in g/d in broiler chickens having received normal feed for 35 days (control: cob+water—T1) or feed with cob mixed with *Spirulina platens/s* protein hydrolyzate (E1) and the polysaccharide extract of *Ascophyllum nodosum* (E2) at 200 g/T of food of E1+100 g/T of food of E2 (T2), 600 g/T of E1+100 g/T of E2 (T3), 1000 g/T of E1+100 g/T of E2 (T4), 600 g/T of E1+500 g/T of E2 (T5) or 600 g/T of E1+500 g/T of E2+Aroma (T6) respectively under the conditions of Example 4. The letters a, b or c associated with the numbers indicate the significant differences between treatments at 5% confidence. The percentage values indicate the range of improvement over the control.

FIG. 13 represents the final live weight at D35 in grams of broiler chickens having received the normal feed (control: cob+water—T1) or a feed provided with cob mixed with the *Spirulina platens/s* protein hydrolyzate (E1) and the polysaccharide extract of *Ascophyllum nodosum* (E2) at 200 g/T of food of E1+100 g/T of food of E2 (T2), 600 g/T of E1+100 g/T of E2 (T3), 1000 g/T of E1+100 g/T of E2 (T4), 600 g/T of E1+500 g/T of E2 (T5) or 600 g/T of E1+500 g/T of E2+Aroma (T6) respectively under the conditions of Example 4. The letters a, b or c associated with the numbers indicate the significant differences between treatments at 5% confidence. The percentage values indicate the range of improvement over the control.

FIG. 14 represents the weight of the thighs at D35 in grams of broiler chickens having received the normal feed (control: cob+water—T1) or a feed provided with cob mixed with the *Spirulina platensis* protein hydrolyzate (E1) and the polysaccharide extract of *Ascophyllum nodosum* (E2) at 200 g/T of food of E1+100 g/T of food of E2 (T2), 600 g/T of E1+100 g/T of E2 (T3), 1000 g/T of E1+100 g/T of E2 (T4), 600 g/T of E1+500 g/T of E2 (T5) or 600 g/T of E1+500 g/T of E2+Aroma (T6) respectively under the conditions of Example 4. The letters a, b or c associated with the numbers indicate the significant differences between treatments at 5% confidence. The percentage values indicate the range of improvement over the control.

FIG. 15 represents the weight of a tibia at D35 in grams of broiler chickens having received the normal feed (control: cob+water—T1) or a feed provided with cob mixed with the *Spirulina platensis* protein hydrolyzate (E1) and the polysaccharide extract of *Ascophyllum nodosum* (E2) at 200 g/T of food of E1+100 g/T of food of E2 (T2), 600 g/T of E1+100 g/T of E2 (T3), 1000 g/T of E1+100 g/T of E2 (T4), 600 g/T of E1+500 g/T of E2 (T5) or 600 g/T of E1+500 g/T of E2+Aroma (T6) respectively under the conditions of Example 4.

FIG. 16 represents the number of total bacteria, bifidobacteria spp, lactobacilli spp, Enterobacteriaceae, *Clostridium jejuni, Escherichia. Coli-shigella, salmonella* spp and *Clostridium perfringens* at D35 in the caecum of chickens in log/mg of freeze-dried dry caecum in broiler chickens having received the normal feed (control: cob+water—T1) or a feed provided with cobs mixed with *Spirulina platensis* protein hydrolyzate (E1) and the polysaccharide extract of *Ascophyllum nodosum* (E2) at 200 g/T of food of E1+100 g/T of food of E2 (T2), 600 g/T of E1+100 g/T of E2 (T3), 1000 g/T of E1+100 g/T of E2 (T4), 600 g/T of E1+500 g/T of E2 (T5) or 600 g/T of E1+500 g/T of E2+Aroma (T6) respectively under the conditions of Example 4.

EXAMPLE 1: PREPARATION OF EXTRACTS

Example 1a: *Spirulina* Extract (E1)

100 g of raw dehydrated *spirulina* (*Spirulina platensis*) in powder form having a protein content greater than or equal to 60% and a Phycocyanin content greater than or equal to 8% is extracted by maceration in 900 g of water at a temperature of 60° C. for a period comprised between 8 hours and 6 hours, more advantageously between 2 hours and 4 hours. The protein extract obtained (liquid) in aqueous solution is hydrolyzed using the enzyme serine subtilisin endoprotease marketed under the trade name Novo-Pro® D at a temperature of 60° C. and at a pH of 8 so as to obtain a *spirulina* protein hydrolyzate.

The composition of raw *spirulina* per 100 g is collected in the following table 1:

TABLE 1

| Constituents | content in g |
| --- | --- |
| Water | 7.10 |
| Dry matter | 92.90 |
| Mineral matter | 6.64 |
| Organic matter | 86.26 |
| Raw protein | 67.50 |

The composition of the protein extract of *spirulina* per 100 g of raw *spirulina* is collected in the following table 2:

TABLE 2

| Constituents | Content in g/l |
| --- | --- |
| Dry matter | 61.0 |
| Mineral matter | 8.7 |
| Organic matter | 52.3 |
| Proteins | 45.2 |
| including Phycocyanin | 10.9 |

The composition in solubilized polypeptides and peptides of the *spirulina* protein hydrolyzate from 100 g of raw *spirulina* is collected in the following table 3:

TABLE 3

| Constituents according to the average weight (MW) in Da | Content in g/l |
|---|---|
| MW > 20 000 Da | 1.4 |
| MW from 10 000 to 20 000 Da | 0.6 |
| MW from 5 000 to 10 000 Da | 0.4 |
| MW from 1 000 to 5 000 Da | 4.4 |
| MW from 500 to 1 000 Da | 6.8 |
| MW from 150 to 500 Da | 14.1 |
| MW < 150 Da | 17.5 |

The solubilized amino acid composition (MW<150 Da) of the *spirulina* protein hydrolyzate from 100 g of raw *spirulina* is collected in Table 4 below:

TABLE 4

| Constituents according to the average weight (MW) in Da | Content in g/l |
|---|---|
| Aspartic acid | 0.3 |
| Threonine | 0.8 |
| Serine | 0.9 |
| Glutamic acid | 0.7 |
| Proline | <0.2 |
| Glycine | 0.3 |
| Alanine | 1.4 |
| Cystine | <0.2 |
| Valine | 1.2 |
| Methionine | 0.6 |
| Isoleucine | 0.8 |
| Leucine | 2.4 |
| Tyrosine | 1.2 |
| Phenylalanine | 1.4 |
| Histidine | 0.3 |
| Lysine | 1.0 |
| Arginine | 1.6 |

Example 1b: *Ascophyllum Nodosum* Extract (E2)

200 g of raw dehydrated *Ascophyllum nodosum* in powder form is extracted by maceration in 800 g of water at a temperature comprised between 45° C. and 90° C. for a period comprised between 2 hours and 4 hours. The saccharide extract obtained (liquid) is clarified by decantation or draining. The composition of raw *Ascophyllum nodosum* per 100 g is collected in the following table 5:

TABLE 5

| Constituents | content in g |
|---|---|
| Water | 13.5 |
| Dry matter | 86.5 |
| Mineral matter | 26.4 |
| Organic matter | 60.1 |
| Carbohydrates | 54.5 |
| Proteins | 5.6 |
| Cadmium | <1 ppm |
| Lead | <2 ppm |
| Mercury | <0.02 ppm |
| Fluorine | <75 ppm |
| Arsenic | 33.5 ppm |

The composition of clarified liquid *Ascophyllum nodosum* saccharide extract per 100 g of raw *Ascophyllum nodosum* is collected in Table 6 below:

TABLE 6

| Constituents | Content in g/l |
|---|---|
| Dry matter | 143 |
| Mineral matter | 50 |
| Organic matter | 93 |
| Carbohydrates | 86.7 |
| Proteins | 6.3 |
| Cadmium | <1 ppm |
| Lead | <2 ppm |
| Mercury | <0.02 ppm |
| Fluorine | <75 ppm |
| Arsenic | 5.2 ppm |

EXAMPLE 2: STUDY OF THE EFFECT OF THE COMPOSITION ACCORDING TO THE INVENTION ON THE FERMENTATION OF THE RUMEN AND THE DEGRADATION OF THE RATION

The compositions according to the invention comprising:
A content of *spirulina* extract obtained according to Example 1a (E1) corresponding to 50 g/d and a content of *Ascophyllum nodosum* extract obtained according to Example 1b (E2) corresponding to 20 g/d (50+20 g/d E1+E2);
A content of *spirulina* extract obtained according to Example 1a (E1) corresponding to 5 g/d and a content of *Ascophyllum* extract *nodosum* obtained according to Example 1b (E2) corresponding to 10 g/d (5+10 g/d E1+E2);
A content of *spirulina* extract obtained according to Example 1a (E1) corresponding to 5 g/d, a content of *Ascophyllum nodosum* extract obtained according to Example 1b (E2) corresponding to 10 g/d and a lithothamnium content (CalseaPowder Advance CPA) corresponding to 80 g/d in a simple mixture (CPA+E1+E2);
A content of *spirulina* extract obtained according to Example 1a (E1) corresponding to 5 g/d, a content of *Ascophyllum nodosum* extract obtained according to Example 1b (E2) corresponding to 10 g/d and a lithothamne content (CalseaPowder Advance CPA) corresponding to 80 g/d with impregnation of the extracts on the CPA (CPA+E1+E2);
have been tested.
The comparative compositions comprising:
A content of *spirulina* extract obtained according to Example 1a (E1) corresponding to 50 g/d or 5 g/d (50 g/d E1 or 5 g/d E1);
A content of *Ascophyllum nodosum* extract obtained according to example 1b (E2) corresponding to 20 g/d or 10 g/d (20 g/d E2 or 10 g/d E2);
A lithothamne content (CalseaPowder Advance CPA) corresponding to 80 g/d (CPA);
A content of *spirulina* extract obtained according to Example 1a (E1) corresponding to 5 g/d and a content of lithothamne (CalseaPowder Advance CPA) corresponding to 80 g/d in a simple mixture (CPA+E1);
A content of *Ascophyllum nodosum* extract obtained according to Example 1b (E2) corresponding to 10 g/d and a lithothamne content (CalseaPowder Advance CPA) corresponding to 80 g/d in a simple mixture (CPA+E2);
A content of *spirulina* extract obtained according to Example 1a (E1) corresponding to 5 g/d and a content of lithothamnium (CalseaPowder Advance CPA) corresponding to 80 g/d with impregnation of the extract on the CPA (CPA+E1);

A content of *Ascophyllum nodosum* extract obtained according to Example 1b (E2) corresponding to 10 g/d and a lithothamne content (CalseaPowder Advance CPA) corresponding to 80 g/d with impregnation of the extract on the CPA (CPA+E2);

have been tested.

Material and Method

The approach is based on the in vitro fermentation technique developed by the Animal Nutrition Laboratory of the Centre Mondial de l'Innovation Roullier. The principle is based on the incubation of fresh rumen juice from dairy cows mixed with artificial saliva prepared in the laboratory. The compositions to be tested and the ration (winter-fibrous type) are incorporated under conditions similar to reality (anaerobiosis at 39° C.) and with continuous stirring (in order to mimic peristaltic movements). The bacterial flora in the presence of the appropriate substrate reproduces the ruminal fermentation which allows to follow the production of gas as well as the end products such as VFAs, N—NH₃ according to the objectives of the study.

To evaluate the effect of the composition according to the invention on the fermentation of the rumen and the degradation of the ration, rumen juice is taken from 3 fistulated cows fed with a ration based on corn silage, hay and concentrates (cereal mix). To reproduce the physiological conditions, a ration based on corn silage, hay and energy concentrate (50:30:20) is incubated in the inoculum composed of rumen juice and artificial saliva. The rumen juice/artificial saliva ratio is 1:2. Each test takes place over 24 hours with an intermediate follow-up at 6 hours of fermentation. Finally, the initial pH is adjusted to 6.5 to guarantee the physiological conditions of the rumen or to 6.2 to simulate conditions favorable to acidosis, with 80% lactic acid. Each 100 ml flask to be incubated consisted of:

20 ml of filtered rumen juice
    40 ml of artificial saliva (buffer capacity: Buffer substances: Na and ammonium carbonate; Macro-elements: Na, P, K and Mg; Micro-elements: Ca, Mn, Co and Fe)
    0.5 g of substrate ground to 1 mm: the substrate can be a winter ration (50% corn silage+30% hay+20% energy concentrate (made up of 20% wheat, 20% corn, 20% barley, 20% beet pulp, 15% wheat bran and 5% molasses) or an acidogenic ration (33% corn silage+17% soybean cake+50% energy concentrate (consisting of 20% wheat, 20% corn, 20% barley, 20% beet pulp, 15% wheat bran and 5% molasses) and
    The composition to be tested After 6 and 24 hours of incubation at 39.5° C., the flasks are placed in ice to stop the reactions. The pH is measured immediately after leaving the incubator before filtration.

The substrate is separated from the rumen juice by centrifugation (20 min at 4 000 revolutions per min) to recover 50 ml of juice intended for the determination of volatile fatty acids (VFAs) in the medium. The recovered substrate is freeze-dried for 48 hours then ground for the fiber assays (fibers insoluble in neutral detergents (NDF) and fibers insoluble in acid detergents (ADF)).

Continuous recording of the pressure in the flasks allows to determine the volume of gas produced in ml/g of the dry matter (DM). Finally, on the purge of each gas production recording module, a collection bag is adapted to collect a sample to allow analysis of the composition of the gases produced after 24 hours of incubation.

Results

Monitoring of Gas Production:

The fermentation of the substrate by the flora of the rumen leads to the production of gases mainly $CO_2$ and methane ($CH_4$). FIGS. 1, 3 and 4 show the concentration and volume of $CH_4$ produced after 24 hours of fermentation.

The extracts E1 and E2 show a synergistic action on the production of $CH_4$ with reductions of 40% and 36%, respectively for the concentration and the volume, for the highest contributions. The impact is proportional to the application dose with a 16% drop in volume at low doses (FIG. 1). These treatments inhibit the fermentation activity of part of the rumen flora.

The combination of extracts in a simple mixture with CPA (lithothamne) is the most effective treatment for limiting the production of $CH_4$ (−31% by volume) compared to extracts alone or to CPA alone or mixed with one of the extracts (FIG. 3). Modalities have a marked effect on these parameters (p<0.001).

Overall, the combination of extracts impregnated with CPA reduces the volume of $CH_4$ produced during rumen fermentation by 19% (FIG. 4).

Thus, during the fermentation, the production of $CH_4$ is reduced by the addition of the compositions according to the invention. This decrease confirms the direct inhibition of methanogenic bacteria and protozoa. Indeed, the combination of these 2 families is responsible for 9 to 25% of the production of $CH_4$. The addition of the composition according to the invention should allow to limit the energy losses since the production of $CH_4$ leads to approximately 10% loss of the energy consumed by the animal.

Parameters of the Ration

FIG. 2 shows the digestibilities of the dry matter (dDM), ADF (dADF) and NDF (dNDF) after 24 hours of fermentation. The synergistic action of the extracts allows to improve between 20% and almost 40% the degradation of the ration depending on the dose of application and the parameter considered.

The composition according to the invention therefore allows to improve the dDM. The ration is therefore better consumed by the flora of the rumen whether it is cellulolytic or amylolytic. The composition according to the invention also increases the dADF and dNDF. It promotes the degradation and use of the fibers of the ration in this case rich in fodder (80%) with corn silage and hay.

Conclusion

The effect of the composition according to the invention on the fermentation of the rumen and the degradation of the ration under physiological conditions could therefore be evaluated. This composition therefore allows optimal functioning of the rumen via the optimization of ruminal fermentation. It reduces the production of enteric $CH_4$. It therefore probably inhibits part of the flora, the protozoa which are combined with methanogenic bacteria. This defaunation allows to limit $CH_4$ emissions, thus reducing energy losses for the animal, which is essential for the performance of dairy cows.

The composition according to the invention significantly improves the degradation of the ration. Indeed, the digestibilities of the dry matter (DM) and fibers (NDF and ADF) increase compared to the control without supplementation. This product allows better use and degradation of the fiber by the flora of the rumen, the effect of which is proven and reproducible.

On the other hand, the use of E1 and E2 alone shows a less significant effect on the production of $CH_4$ which clearly demonstrates that the use of these compounds alone is not sufficient to significantly improve microbial metabolism and therefore the use of rations.

EXAMPLE 3: STUDY OF THE EFFECT OF THE COMPOSITION ACCORDING TO THE INVENTION ON PIGLETS

The compositions according to the invention comprising:
0.2% by weight of raw *spirulina* (*Spirulina platensis*) and 0.02% by weight of raw *Ascophyllum nodosum* (T3);
0.2% by weight of raw *spirulina* (*Spirulina platensis*) and 0.05% by weight of raw *Ascophyllum nodosum* (T4);
0.2% by weight of raw *spirulina* (*Spirulina platensis*) and 0.1% by weight of raw *Ascophyllum nodosum* (T5);
have been tested.

The comparative compositions comprising:
0.2% by weight of raw *spirulina* (*Spirulina platensis*) (T2);
no algae (control T1);
have been tested.

Material and Method

Farming from 28 to 70 days of age, male piglets only. Two buildings: building 1: 5T×3C×18P—building 2: 5T×3C×18P. 51 (building 1)+51 (building 2)=108 piglets per treatment, that is to say 540 piglets in total (T=Treatment, C=Cages and P=Piglets). Distribution of products throughout the test period. The feed for these piglets consists of a $1^{st}$ age feed then a $2^{nd}$ age feed.

Weaning the piglet is characterized by a reduction in feed intake, a period of anorexia lasting 2 to 4 days inducing, if poorly managed, intestinal lesions that can produce severe inflammation and tissue damage.

Early control of intestinal inflammation is a major challenge in the management of intestinal disorders in piglets during this difficult period of their lives.

Morphometric and functional changes can also be caused by nutritional factors present in certain diets or other products combined with the formulation.

For example, the use of soybean cake in piglet feed can cause fermentation in the intestine as well as diarrhea. Indeed, soybean cake contains antigens that induce severe inflammation and tissue damage. It is for this reason that its inclusion is often restricted in feeds for piglets. These piglets often have damaged intestinal villi leading to poor nutrient absorption.

The objective of this example is to evaluate the effect of supplementation with a composition according to the invention on the immune system (proteins in the blood) and on the morphology of the intestinal villi.

Results

Blood immunity: FIGS. 5 and 6 represent respectively the levels of Beta-1-globulin (serum proteins) and total proteins in the blood of piglets at D 70. β1-globulin is a polypeptide which exists in a free form and a form bound to cell membranes. This polypeptide plays an important role in immune defenses.

It is noted that the amount of blood serum proteins increases (p.val=0.09) with *spirulina* alone or in a mixture with 0.02% and 0.05% of *Ascophyllum*. To this end, a significant increase is observed up to 19.7% for the composition containing 0.2% raw *Spirulina*+0.02% raw *Ascophyllum* or 12.8% for the composition containing 0.2% raw *Spirulina*+0.05% raw *Ascophyllum*. The composition containing 0.2% raw *Spirulina*+0.02% raw *Ascophyllum* therefore seems to be the most effective.

Similarly, the amount of total blood protein increases with *spirulina* alone or with the composition containing 0.2% raw *Spirulina*+0.02% raw *Ascophyllum*. An interesting effect is particularly observed for the composition T3 (0.2% raw *Spirulina*+0.02% raw *Ascophyllum*) with an increase of 4.3%.

Length of intestinal villi at D70: Many morphological studies of the gastrointestinal mucosa have been undertaken to understand changes in intestinal functioning during piglet development and particularly around weaning. Weaning induces rapid, transient and significant changes in the physiology of the piglet but also a maturation of the intestinal capacities.

In this study, morphometric measurements were performed at D70 on small intestine samples and the results are shown in FIG. 7.

Supplementation with the composition according to the invention increased the length of the jejunal villi without major effect on the duodenal villi.

The treatments containing the highest doses of *Ascophyllum* increase (p.val=0.08) the length of the villi of the jejunum by up to 15.4% with the composition containing 0.2% raw *Spirulina*+0.05% raw *Ascophyllum* (the most interesting composition).

Supplementation with a composition according to the invention can therefore modulate the inflammatory response via the increase in jejunal villi via the appearance of simple sugars probably or peptides (resulting from enzymatic reactions in specific absorption sites) which thus avoid damage associated with post-weaning nutritional stress.

Conclusions on Health and General Conclusion:

Positive effects with the composition according to the invention have been observed in particular on the length of the villi of the jejunum of piglets.

A modulation of the immune response on the integrity of the intestinal mucosa was thus observed in these experiments with an effect of the supplementation with the composition according to the invention in a farming of male piglets only from 28 to 70 days of age (post-weaning).

The results obtained are interesting because the daily consumption is very different between the different compositions between D28 and D42 (period of $1^{st}$ age) with a very significant p. Value (0.004) as shown in FIG. 8. Indeed, the consumption of the food was reduced either because of the transition period (post-weaning) in these test batches, or probably because of the taste or the smell of the composition according to the invention; However, despite this reduction in feed intake, the results remain positive on health, especially for the composition T3 (0.2% raw *Spirulina*+0.02% raw *Ascophyllum*) whose average daily gain (ADG) is equivalent to the control (see FIG. 9) while being correlated with a very low daily consumption (−11.8%/T1).

EXAMPLE 4: STUDY OF THE EFFECT OF THE COMPOSITION ACCORDING TO THE INVENTION ON BROILER CHICKENS

The compositions according to the invention comprising:
200 g of *Spirulina* extract obtained according to Example 1a (E1)/T of food+100 g of *Ascophyllum* extract obtained according to Example 1b (E2)/T of food (T2);
600 g/T of E1+100 g/T of E2 (T3);
1000 g/T of E1+100 g/T of E2 (T4);
600 g/T E1+500 g/T of E2 (T5);
600 g/T E1+500 g/T of E2+0.05 g/kg of aroma marketed by Kaesler (T6);
have been tested.

The comparative compositions comprising:

no algae and water (control T1);

have been tested.

Material and Method

The feed has been formulated to meet 95% of the nutritional requirements of male chickens of Aviagen Ross 308 strain. It was distributed ad libitum for 35 days.

The test consisted of 6 food treatments comprising cobs and one of the compositions indicated above (T1 to T6). These treatments were distributed throughout the farming period.

A set of parameters attributable to the intestine were recorded during (D7 and D15) and at the end of the test on D35.

Results

The parameter noted in the start-up (D7) and growth (D15) phase is the histological study of the intestinal mucosa. The length of the villi and the depth of the crypts at the duodenum, the jejunum and the ileum were measured. Thus the study of the intestinal morphology at the start showed a tendency (p.val=0.16) towards an increase in the depth of the duodenal crypts at D7 (FIG. 11). The depth of the crypts of the chicks of the treatment T4 (1000 g/T E1+100 g/T E2) shows an increase of 9% compared to the control treatment T1. Similar results could be observed on the same farming phase in a previous test which had indeed demonstrated a tendency towards an increase in the length of the villi (p.val=0.11) and the depth of the duodenal crypts (p.val=0.15) on D7, of chicks having received the composition according to the invention in their drinking water (FIG. 12). At equal dose of *Ascophyllum* extract in water (0.02%), crypts and villi have increased with decreasing dose of *spirulina* extract from 0.1 to 0.02%.

Contrary to the contribution in the food, it would seem that the dose of *spirulina* extract brought in the drinking water does not need to be maximum to support the growth of the villi and the depth of the crypts. The dose will therefore depend on the form of intake selected.

These variations in villus length and crypt depth are a good indicator of the nutrient digestion and absorption capacities of the small intestine. Indeed, even more importantly, the development of the intestinal mucosa takes place very quickly after hatching in the first 7 days of the animal's life. In particular, this development takes place at the beginning of the intestine in the duodenum, although the levels are different between intestinal segments. Thus, the volume of villi in the duodenum reaches a plateau after 7 days while it continues to grow in the jejunum and ileum after 7 days. However, live weight at 42 days of age is correlated with live weight at 21 days, itself correlated with live weight at 7 days, itself in relation to the good absorptive capacity at the start of life. Wide villi, more numerous microvilli and more active epithelial cells at the duodenum and jejunum in the early life of chickens suggest a large absorptive surface area and active intestinal function, which lead to faster and better growth of chickens after hatching. The performance data (weight and food consumption) were recorded during the finishing period at D27 and D35. Thanks to this, the consumption index (CI) and the average daily gain (ADG) of the chickens could be calculated. The finishing performances measured between D27 and D35 thus showed an improvement in the $ADG_{27-35}$ over this period with the addition of the composition according to the invention (FIG. 12). Over the last farming week, the addition of the mix of extracts, in particular the dose of 600 g/T of E1 combined with 100 or 500 g/T of E2 allowed to increase the $ADG_{27-35}$ by approximately 5.4% relative to the water control (p.val=0.03). Similarly, this test demonstrated an increase in final live weight (LW) at D35 (FIG. 13). In the same way as for the $ADG_{27-35}$, the LW at D35 is improved by approximately 2.7% with a dose of 600 g/T of *spirulina* extract (E1) combined with a dose of 100 or 500 g/T of *Ascophyllum* extract (E2). This improvement in the final LW is therefore due to an increase in the ADG over the last farming week. This seems to indicate that in the case of a distribution of extracts in the food, this should be done over the entire farming period to obtain this result.

In order to understand where this improvement in the final LW came from, correlations were carried out between this LW and the weight of the organs and parts sampled and weighed during this test. A correlation of 94% was measured between the LW and the weight of the thighs of the chickens. An average correlation of 50% was measured between the LW and tenderloins or tibias. The pieces of meat, in particular the thighs and the skeleton therefore seem to explain the weight gain.

The weighing of the pieces most valued in human food (tenderloin and thighs) showed a tendency (p.val=0.17) to increase the weight of the thighs according to the treatments (FIG. 14). FIG. 14 therefore shows that the chickens having received 600 g/T of E1+100 g/T of E2 have a higher thigh weight of almost 3% compared to the water control. The chickens of this treatment, which are a little heavier at the end of farming, also have a higher thigh weight than the chickens of the other treatments. As shown in FIG. 15, tibial weight also tended to increase (p.val=0.18) by almost 4% with the intake of 600 g/T E1+100 g/T E2. Such a predisposition is relatively important in the broiler whose genetics selected with precision during these last decades resulted in an improvement of the growth capacities of the animals. The growth rate of chickens has indeed increased by 300% in fifty years, going from 25 g/day to 100 g/day. This progress, however, resulted in the weakening of their legs, too weak to support such a weight so quickly. After forty days of farming, this can represent nearly 30% of chickens with locomotion problems or an inability to walk. The growth of these animals is then slowed down, the chickens no longer having access to the feeder. Indirectly, these problems represent an economic loss for farmers. It is therefore important that the bone structure of the tibias is of good quality since it is a component that will affect the farmers' wages.

The parameters recorded during the finishing phase (D35) or at slaughter are:

at slaughter, samples of cecal content were also taken in order to count the following bacterial populations by qPCR:

Beneficial Populations:

Lactobacilli

Bifidobacteria

Pathogenic Populations:

*Clostridium perfringens*

*Salmonella* spp

*Escherichia. Coli-shigella*

*Clostridium jejuni*

Enterobacteriaceae

Total Bacteria

The bacterial populations of the cecum were counted. The results showed modifications in these populations with the addition of the composition according to the invention (FIG. 16).

FIG. 16 thus shows that the chickens having received 600 g/T of E1+100 g/T of E2 (T3) show the lowest development of bacterial populations. This is particularly true for bifido-bacteria, lactobacilli, enterobacteria, *E. coli-shigella* and *salmonella*.

As a result, the total number of bacteria in the cecum is 8.59 Log 10 for the chickens in this treatment when this number is comprised between 8.60 and 9.05 Log 10 for the other treatments. Treatment with aroma is not recommended here because it promotes the development of these populations.

A discriminant analysis coupled with a comparison of the distances of this analysis by Fisher's method revealed that the populations of the control and the treatment T3 are significantly different (p.val=0.04).

Furthermore, it will be noticed that all the effects observed so far between treatments T2, T3 and T4, at a constant dose of *Ascophyllum* extracts but at an increasing dose of *spirulina* extract, do not follow a linear regression (improvement of parameters with the dose of *spirulina* extract) but a plateau quadratic regression. Thus, the dose of *spirulina* extract does not need to be maximum for effects to be observed. Conversely, a too high dose of *spirulina* extract could negatively affect the results.

General Conclusion

The test presented here, supplemented with the results of a previous test, demonstrated the benefit of adding either a dose of 0.02% of *spirulina* extract+0.02% of *Ascophyllum* extract in chicken drinking water at the start from D0 to D7, or a dose of 1000 g of *spirulina* extract+100 g of *spirulina* extract/T of chicken feed at the same age. A food supplement at the start could indeed be proposed in the sense that it favors the increase in the length of the villi and the depth of the duodenal crypts. This effect is also a good indicator of the digestion of nutrients and the absorption capacities of the small intestine, functions that are relatively important at the start because they can condition the weight gain of the animals and the modulation of immunity throughout their life. The recommended dose will depend on the form of intake: in drinking water or in food.

In the same way, this food supplement could continue to be distributed until the end of the farming period at a dose of 600 g of *spirulina* extract+100 g of *Ascophyllum* extract/T of food in order to obtain a higher final LW which is explained by a greater weight of the thighs. This dose also allows to obtain a higher tibia weight favorable to a better locomotion and a reduction in the total caecal bacterial populations including the pathogenic bacteria E coil *shigella*, enterobacteria and *salmonella*.

EXAMPLE 5: STUDY OF THE EFFECT OF THE COMPOSITION ACCORDING TO THE INVENTION ON THE FERMENTATION OF THE RUMEN AND THE DEGRADATION OF THE RATION

The compositions according to the invention comprising:
an *Ascophyllum nodosum* extract obtained according to Example 1b (AN-E);
an extract of *Spirulina platensis* obtained according to Example 1a (SP-E);
a mixture (SAT-E) of 32% by weight of *spirulina* extract obtained according to Example 1a (E1) and 68% by weight of *Ascophyllum nodosum* extract obtained according to Example 1b (E2);
*Spirulina platensis* in raw form (SP-B);
*Ascophyllum nodosum* in raw form (AN-B);

a mixture (SAT-B) of 32% by weight *Spirulina platensis* in raw form and 68% by weight of *Ascophyllum nodosum* in raw form.

The doses tested for each of the mixtures are from 1 to 30 g/d (low).

The method is the same as that of Example 1 (in vitro fermentation technique developed by the Animal Nutrition Laboratory of the Centre Mondial de l'Innovation Roullier).

Results:

They are collected in tables 7 and 8 below:

TABLE 7

| effects on methane production | | | | | |
|---|---|---|---|---|---|
| | dose | [CH$_4$] % | Volume of CH$_4$ (ml/g of DM) | diff in [CH$_4$] | diff in volume |
| Control | None | 4.4 | 6.5 | | |
| AN-B | Low | 4.1 | 6.24 | −5% | −4% |
| SAT-B | Low | 3.1 | 4.83 | −29% | −26% |
| SP-B | Low | 3.9 | 5.69 | −10% | −12% |
| AN-E | Low | 4.2 | 6.20 | −4% | −5% |
| SAT-E | Low | 3.7 | 5.75 | −15% | −12% |
| SP-E | Low | 4.2 | 5.92 | −4% | −9% |

A significant effect of the low application dose (<30 g/l) is observed: $p<0.001$ on the CH$_4$ concentration of the gas for the mixture, which is higher than that of the algae alone, which clearly demonstrates a synergy.

The mixture of raw algae is even more interesting than the mixture of algae extract (−29% on the concentration and −26% on the volume).

TABLE 8

| effects on the digestibility of the ration (dDM): | | | |
|---|---|---|---|
| | dose | dDM % | diff vs control |
| Control | None | 49 | |
| AN-B | Low | 49 | 0% |
| SAT-B | Low | 54.2 | 11% |
| SP-B | Low | 50.3 | 3% |
| AN-E | Low | 49.1 | 0% |
| SAT-E | Low | 53.2 | 8% |
| SP-E | Low | 48.5 | −1% |

The composition according to the invention containing the mixture of algae according to the invention, whether in their raw form or as an extract, show a slight improvement in the dDM, unlike the algae alone. The synergistic effect will potentially be more marked in vivo with daily consumption.

In addition, no negative effect on fermentation was observed at the doses tested.

The invention claimed is:

1. A composition for the nutrition or drink of a ruminant mammal, comprising a combination of *spirulina* and *Ascophyllum nodosum*, wherein the *spirulina* is in the form of a protein hydrolysate and *Ascophyllum nodosum* is in the form of a polysaccharide extract.

2. The composition according to claim 1, wherein the *spirulina/Ascophyllum nodosum* weight ratio is within the range 0.02-100.

3. The composition according to claim 1, which comprises between 0.01 and 0.5% by weight relative to the total weight of the composition of the *spirulina*.

4. The composition according to claim 1, which comprises between 0.05 and 0.5% by weight relative to the total weight of the composition of *Ascophyllum nodosum.*

5. The composition according to claim 1, which further comprises lithothamnium.

6. A method for improving the zootechnical performance of a ruminant mammal, comprising administering to a ruminant mammal in need thereof the composition according to claim 1.

7. A method for reducing the emission of methane from a ruminant mammal, comprising administering to a ruminant mammal in need thereof the composition according to claim 1.

8. A method for increasing the digestibility of the dry matter and fibers and/or for improving the consumption index and/or the dietary efficiency and/or for promoting weight gain and/or for increasing the intensity of fermentation and of microbial metabolism and/or for inhibiting flora protozoa and/or for reducing the degradation of proteins and/or for orienting the fermentation towards the production of volatile fatty acids, in a ruminant mammal, comprising administering to a ruminant mammal in need thereof the composition according to claim 1.

9. A method for improving the quality of the meat and/or the growth performance and/or the well-being of a ruminant mammal, comprising administering to a ruminant mammal in need thereof the composition according to claim 1.

10. A method for improving the intestinal health and/or the intestinal well-being and/or the immune system and/or the bone mineralization and/or the quality of the bone structure and/or as an antibacterial in a ruminant mammal, comprising administering to a ruminant mammal in need thereof the composition according to claim 1.

* * * * *